US011119062B2

United States Patent
Sondergeld et al.

(10) Patent No.: US 11,119,062 B2
(45) Date of Patent: Sep. 14, 2021

(54) METHOD AND ASSEMBLY FOR MEASURING DIFFUSION IN NANOPOROUS MEDIA

(71) Applicant: The Board of Regents of the University of Oklahoma, Norman, OK (US)

(72) Inventors: Carl H. Sondergeld, Norman, OK (US); Chandra S. Rai, Norman, OK (US); Son T. Dang, Norman, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 92 days.

(21) Appl. No.: 16/549,836

(22) Filed: Aug. 23, 2019

(65) Prior Publication Data

US 2020/0064284 A1 Feb. 27, 2020

Related U.S. Application Data

(60) Provisional application No. 62/721,775, filed on Aug. 23, 2018.

(51) Int. Cl.
*G01N 24/08* (2006.01)
*G01R 33/28* (2006.01)
*G01R 33/46* (2006.01)
*G01R 33/32* (2006.01)
*G01R 33/30* (2006.01)

(52) U.S. Cl.
CPC ......... *G01N 24/081* (2013.01); *G01R 33/283* (2013.01); *G01R 33/30* (2013.01); *G01R 33/323* (2013.01); *G01R 33/46* (2013.01)

(58) Field of Classification Search
CPC ............ G01N 24/081; G01N 33/0047; G01N 21/3504; G01N 2021/3595; G01N 33/24; G01R 33/283; G01R 33/46; G01R 33/323; G01R 33/30
See application file for complete search history.

(56) References Cited

U.S. PATENT DOCUMENTS

2019/0086312 A1* 3/2019 Kwak .................... G01N 11/00

OTHER PUBLICATIONS

Hill, E. S., et al.; "Rate of Solution of Methane in Quiescent Liquid Hydrocarbons"; Industrial and Engineering Chemistry; 26:12 (1934) 1324-1327.
Bertram, E. A., et al.; "Rates of Solution of Gases in Oils: Rate of Solution of Methane in Filling Spaces between Sand Grains"; Industrial and Engineering Chemistry; 28:3 (1935) 316-318.
Wicke, E., et al.; "Die Oberflachendiffusion von Kohlendioxyd in aktiven kohlen"; Kolloid Zeitshrift; 97:2 (1941) 135-151.
Reamer, H. H., et al.; "Diffusion Coefficients in Hydrocarbon Systems: Methane-Decane-Methane in Liquid Phase"; Industrial and Engineering Chemistry; 48:2 (1956) 275-282.
Evans, R. B., et al.; "Gaseous Diffusion in Porous Media at Uniform Pressure"; J. Chem. Phys.; 35 (1961) 2076-2083.

(Continued)

*Primary Examiner* — Susan S Lee
(74) *Attorney, Agent, or Firm* — Hall Estill Law Firm

(57) ABSTRACT

Methods, apparatus, and assembly for measuring gas diffusion through tight (nanoporous) rock samples such as shale, and tortuosity of such rock samples.

21 Claims, 12 Drawing Sheets

(56) References Cited

OTHER PUBLICATIONS

Pandey, G. N., et al.; "Diffusion of Fluids Through Porous Media with Implications in Petroleum Geology"; The American Association of Petroleum Geologists Bulletin; 58:2 (1974) 291-303.

Chen, L. L. Y., et al.; "Binary Gas Diffusion of Methane-Nitrogen Through Porous Solids"; AIChE Journal; 23:3 (1977) 336-341.

Riazi, M. R.; "A new method for experimental measurement of diffusion coefficients in reservoir fluids"; Journal of Petroleum Science and Engineering; 14 (1996) 235-250.

Garrouch, A. A., et al.; "Using Diffusion and Electrical Measurements to Assess Tortuosity of Porous Media"; Ind. Eng. Chem. Res.; 40 (2001) 4363-4369.

Jamialahmadi, M., et al.; "Diffusion coefficients of methane in liquid hydrocarbons at high pressure and temperature"; Journal of Petroleum Science and Engineering; 53 (2006) 47-60.

Ballard, B. D., et al.; "Quantitative Mineralogy of Reservoir Rocks Using Fourier Transform Infrared Spectroscopy"; SPE International (2007) 8 pages.

Livanos, G., et al.; "Deconvolution of petroleum mixtures using mid-FTIR analysis and non-negative matrix factorization"; Measurement Science and Technology; 27 (2016) 13 pages.

Chen, M., et al.; "Methane diffusion in shales with multiple pore sizes at supercritical conditions"; Chemical Engineering Journal; 334 (2018) 1455-1465.

Wallace, W.; "Methane: Infrared Spectrum"; NIST Mass Spectrometry Data Center; NIST Chemistry WebBook, SRD 69; (2018) 3 pages.

\* cited by examiner

METHOD AND ASSEMBLY FOR MEASURING DIFFUSION IN NANOPOROUS MEDIA

CROSS-REFERENCE TO RELATED APPLICATIONS

The present application claims priority under 35 U.S.C. § 119(e) to U.S. Ser. No. 62/721,775, filed Aug. 23, 2018, the entirety of which is hereby expressly incorporated herein by reference.

BACKGROUND

Miscible Gas Injection has been proven to be amongst the few successful Enhanced Oil Recovery (EOR) techniques, which can be applied in unconventional reservoirs. Recent reports from oil and gas companies suggest this process can enhance 30% up to 70% of current recovery methods. An effective and economical project depends on an understanding of gas transportation during both injection and flowback. Previous modeling and theoretical investigations have shown that diffusion could be one of dominant transport mechanisms in low permeability shales (nanoporous media).

Hill and Lacy [1], Bertram and Lacy [2], and Reamer et al., [3] have shown that the rate of dissolution of methane in a body of hydrocarbon liquid is controlled primarily by the rate of diffusion of dissolved gas from the gas-liquid interface into the body of the liquid phase. On the other hand, the tortuous features of porous media also govern how fast gas is injected into a matrix. Therefore, it is critical to understand the diffusion processes in any gas injection process in oil reservoirs.

Effective diffusion measurements in both dry and saturated porous media have been well established, although the availability of measurement data is limited (Chen [4], Pandey et al., [5]). Many different methods utilizing secondary parameters, including pressure decay (Chen et al., [6]) or resistivity (Garrouch et al., [7]), have been used to capture diffusion characteristics. However, the most direct technique to measure a diffusion rate has been the method of Wicke and Kallenbach [8], in which nitrogen is flowed across one face of a cylindrical porous media, and methane is flowed across the other face. Equation (1) was developed by Evans et al., [9] to back-calculate the diffusion rate by monitoring the change in fluid composition on both sides of the porous media.

$$D_e = \frac{N_n \alpha RTL}{PA \ln\left(1 - \frac{\alpha Y_{nf}}{1 - \alpha Y_{ni}}\right)} \quad \text{Eqn. 1}$$

$$\text{where } \alpha = 1 - \frac{N_m}{N_n}$$

and where $D_e$ is an effective diffusion coefficient; $N_a$ and $N_m$ are respectively a molar diffusion rate of nitrogen and methane, mole/s; T is an absolute temperature, °K; L is a rock sample length, cm; R is a gas constant; P is a pore pressure, cm Hg; A is a cross-sectional area, $cm^2$; $Y_{nf}$ and $Y_{ni}$ are respectively a nitrogen mole fraction at a final and an initial point.

Most diffusion rates computed or measured from previous methods for conventional rocks provide reasonably consistent outcomes. However, for unconventional tight rock formations, like shale formations, there are drawbacks from each of the previous methods. One common method for measuring diffusion rates is monitoring pressure decay while injecting gases into a saturated rock sample. One of the assumptions to validate this method is that the instant pressure transmits from the borders of the sample to the center of the sample. However, this is a very weak assumption for tight rocks. Wicke and Kallenback's method theoretically can be applied for tight rocks; however, the practical difficulty of this technique lies with how fluid composition should be examined without flow interference. Small transmissibility characteristics of shales make conventional fluid sampling impossible. Moreover, the time-discrete fluid sampling makes it challenging to capture breakthrough time.

Diffusion between any two compounds is governed by the contrast of the concentration of these two compounds at any location in the system, not by the pressure gradient. This is a slow process, but is an important transport mechanism in low permeability porous media, such as shale rocks. To estimate an effective diffusion coefficient, Fick's second law of diffusion is typically applied, using a profile of the concentration of a compound as a function of time. For conventional rock with a big pore scale, scientists extract fluid samples along a gas transportation path, and using independent analytical methods, dominantly gas chromatography, estimate the concentration of the components. The disadvantage of this technique is that interference occurs during gas transportation, which can make the diffusion coefficient estimation incorrect. Furthermore, for microporous media with a small pore volume, the change in concentration as function of time is very small, which makes the extraction method unfeasible. Another method to estimate rock tortuosity is measuring the resistivity of a brine-saturated core sample. However, this technique was developed for conventional rocks, with a large pore scale and clean sand. However, shale rocks involve a nano-scale porous media and rich clays. Another disadvantage of this technique is that cracks in the rock samples can cause inaccurate results.

Previous diffusion measurement data on sandstones, Chen et al., [10], suggest that a diffusion factor (DF), a ratio of the effective diffusion coefficient across a porous media to the effective diffusion coefficient across an open space, is a reverse function of a tortuosity of the rock samples (porous media).

Many previous studies have been done on bulk methane-liquid diffusion. Riazi et al., [11] developed a method for determining diffusion coefficients of gases in liquids at a constant volume and temperature using a PVT cell. Jamialahmadi et al., [12] proposed an interesting approach using an oil swelling factor as a function of time to estimate a methane diffusion rate into different alkanes at a high pressure and a high temperature. However, despite the importance of the diffusion rate as a factor in transport mechanisms in rock formations such as shales, measurements of diffusion coefficients in a microporous rock are not currently available.

BRIEF DESCRIPTION OF THE DRAWINGS

The accompanying drawings, which are incorporated in and constitute a part of this specification, illustrate one or more implementations described herein and, together with the description, explain these implementations. The drawings are not intended to be drawn to scale, and certain features and certain views of the figures may be shown exaggerated, to scale or in schematic in the interest of clarity and conciseness. Not every component may be labeled in every drawing. Like reference numerals in the figures may represent and refer to the same or similar element or function.

DETAILED DESCRIPTION

Figure 1:
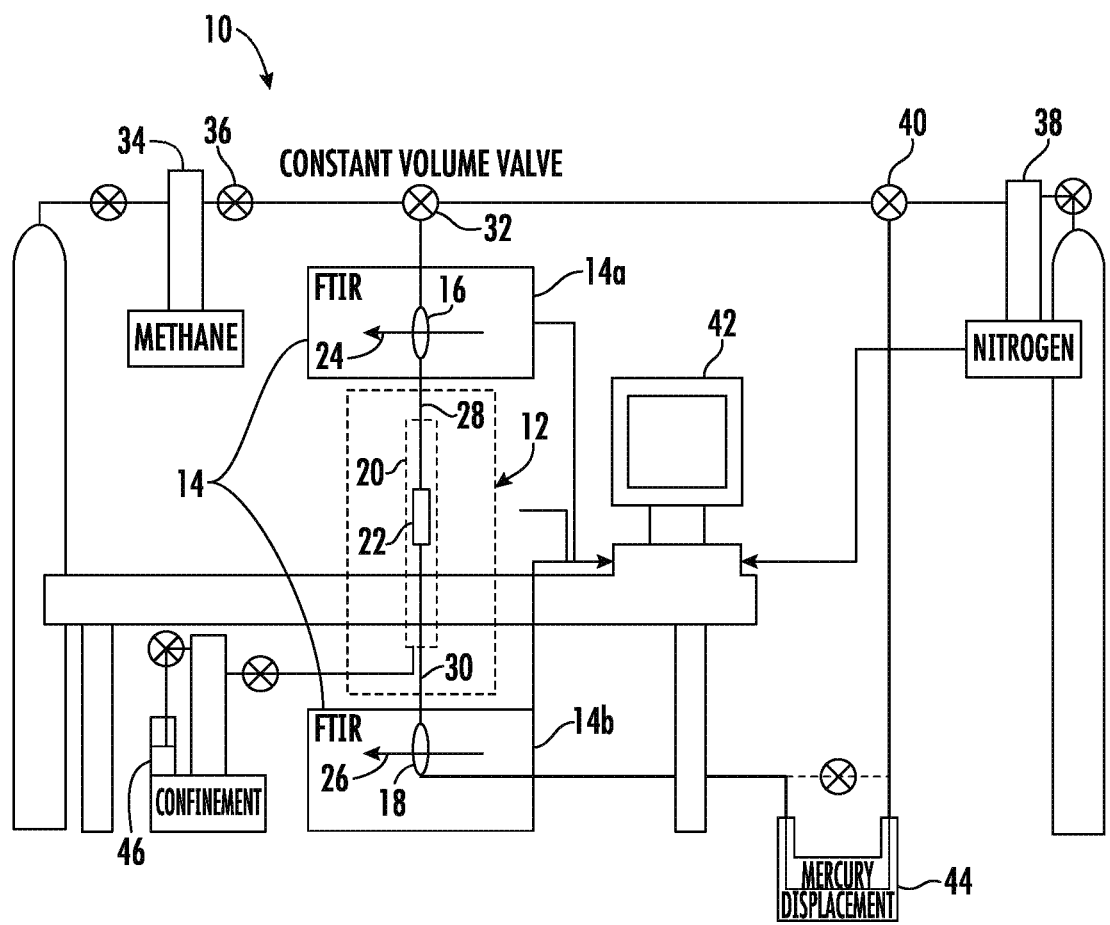
FIG. 1 shows a schematic of a diffusion assembly, in which a porous media sample was filled with nitrogen for 24 hours, then methane was diffused through the nanoporous media sample when a constant volume valve was opened. A mercury displacement pump was used to keep the system under a constant pore pressure throughout the diffusion process.

In certain embodiments, the present disclosure is directed to methods and apparatus for estimating an effective diffusion coefficient of methane through liquid saturated tight rock samples. Such techniques for measuring diffusion in tight rock formations, such as shale formations, are currently unavailable, due at least in part to the generally small pore volume in tight rock formations. The present disclosure therefore identifies a novel approach to measurement of the effective diffusion coefficient and tortuosity of gas compounds in tight (nanoporous) rock formations, such as shale.

Before describing various embodiments of the present disclosure in more detail by way of exemplary description, examples, and results, it is to be understood as noted above that the present disclosure is not limited in application to the details of methods and apparatus as set forth in the following description. The present disclosure is capable of other embodiments or of being practiced or carried out in various ways. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the embodiments of the present disclosure may be practiced without these specific details. In other instances, features which are well known to persons of ordinary skill in the art have not been described in detail to avoid unnecessary complication of the description.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

All patents, published patent applications, and non-patent publications mentioned in the specification are indicative of the level of skill of those skilled in the art to which the present disclosure pertains. All patents, published patent applications, and non-patent publications (e.g., articles) referenced in any portion of this application are herein expressly incorporated by reference in their entirety to the same extent as if each individual patent or publication was specifically and individually indicated to be incorporated by reference.

As utilized in accordance with the methods and apparatus of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, includes ranges of 1-20, 10-50, 50-100, 100-500, and 500-1,000, for example.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the terms "about" or "approximately" are used to indicate that a value includes the inherent variation of error. Further, in this detailed description, each numerical value (e.g., temperature or time) should be read once as modified by the term "about" or "approximately" (unless already expressly so modified), and then read again as not so modified unless otherwise indicated in context. As noted, any range or consecutive set of numbers listed or described herein is intended to include, implicitly or explicitly, any number within the range or set of numbers, including fractions and whole numbers, including the end points, and is to be considered as having been so stated. For example, "a range from 1 to 10" is to be read as indicating each possible number, particularly integers and fractions, along the continuum between about 1 and about 10. Thus, even if specific data points within the range, or even no data points within the range, are explicitly identified or specifically referred to, it is to be understood that any data points within the range are to be considered to have been specified, and that the inventors possessed knowledge of the entire range and the points within the range. The use of the term "about" or "approximately" may mean a range including ±10% of the subsequent number unless otherwise stated.

As used herein, the term "substantially" means that the subsequently described parameter, function, event, or circumstance completely occurs or that the subsequently described parameter, function, event, or circumstance occurs to a great extent or degree. For example, the term "substantially" means that the subsequently described parameter, function, event, or circumstance occurs at least 75% of the time, at least 80% of the time, at least 85% of the time, at least 90% of the time, at least 91% of the time, or at least 92% of the time, or at least 93% of the time, or at least 94% of the time, or at least 95% of the time, or at least 96% of the time, or at least 97% of the time, or at least 98% of the time, or at least 99% of the time, or means that the dimension or measurement is within at least 75%, or at least 80%, or at least 85%, or at least 90%, or at least 91%, or at least 92%, or at least 93%, or at least 94%, or at least 95%, or at least 96%, or at least 97%, or at least 98%, or at least 99%, of the referenced dimension, function, parameter, or measurement (e.g., length).

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment. Features of any of the embodiments disclosed herein may be combined with features of any of the other embodiments disclosed herein to create a new embodiment.

The term "combining", where used herein in relation to values of two or more parameters, means performing a mathematical operation on the two or more parameter values.

Where used herein the term "oil field service" is intended to refer to an operation at a natural gas production site and/or a petroleum (oil) production site. The term "petrophysical" is intended to refer to a parameter related to the physical and/or chemical properties of a rock or rock formation, particularly in regard to the interaction of the rock or rock formation with a fluid. Where used herein the term "unconventional," when applied to a subterranean formation, refers to a underground reservoir of an oil or natural gas (unconventional oil or natural gas) which requires a stimulation treatment in addition to a drilling operation. Such stimulation treatments include, but are not limited to, fracturing, perforation, acidizing, and staging. Where used herein, the term nanoporous refers to materials (media), such as shales, having an average pore diameter size in a range of 1 nm to 1000 nm, 1 nm to 900 nm, 1 nm to 800 nm, 1 nm to 700 nm, 1 nm to 600 nm, 1 nm to 500 nm, 1 nm to 400 nm, 1 nm to 300 nm, 1 nm to 200 nm, or 1 nm to 100 nm.

Returning now to the description of embodiments of the present disclosure an effective diffusion between methane versus nitrogen were simultaneously measured with Infrared Spectroscopy (IR) methods. The IR methods captured a change in a methane concentration and a nitrogen concentration at a gas inlet (input end) and a gas outlet (output end) of a gas flooding system with a tight rock sample as a function of time. The difference in the effective diffusion coefficient with and without the tight rock sample (microporous media), provides a tortuosity of the tight rock sample. In the end, a simulation model was established based on an experimental setup to back-calculate a diffusion rate. The effective diffusion coefficient of methane through a liquid saturated porous matrix can be estimated from a bulk methane-liquid diffusion coefficient and a diffusion factor of the porous media. Another advantage of the disclosed process is that it does not rely on or require fluid extraction for analysis. Therefore, no flow interference is present during the diffusion procedure, which could introduce errors into the results. The disclosed method enables conditions close to reservoir conditions (high temperature, high pressure), and records precisely small changes in the IR absorbable gas concentration. Moreover, different fluid components can absorb light at different ranges of wavelength, making the experimental setup applicable to multi-component diffusion, not just binary diffusion.

An IR absorbance intensity is very sensitive to a small range of gas concentrations, which makes the presently disclosed technique applicable to analyzing gas transportation through a small pore scale material. The IR absorbance intensity is governed by Beer-Lambert's law, which states that an absorbance is linearly proportional to an IR absorbable gas concentration, which means calibration can be completed easily. Conversion from the IR absorbance intensity to the IR absorbable gas concentration is used to back-calculate the effective diffusion coefficient and the tortuosity of the porous media.

As noted, in the microporous media, the concentration exchange rate of fluid components is very small. In the presently disclosed method, the IR transparent window cells are located inline of the gas transportation path. A light beam with a certain range of wavelength is continuously shot across the IR transparent window cells. In certain embodiments, the IR transparent window cells may be constructed from sapphire or zinc selenide (ZnSe), which are transparent to an absorbance range of hydrocarbon molecules, and strong enough to withhold a pressure within the IR transparent window cells (up to 2500 psi for a ZnSe cell, and 5000 psi for a sapphire cell).

The disclosed technique can be used in many petrophysics laboratories to accurately estimate a shale diffusion coefficient and the tortuosity which controls oil and gas extraction. These two factors are important for any reservoir model, but are not available in any commercial core measurement techniques. This method can also be applied in refinery research, in terms of understanding gas transportation in zeolite catalysts, a microporous media. Further, the IR absorbance intensity versus the gas concentration conversion can be used in multiple industries, for example, to evaluate the quality of an engine emission system.

IR methods have been applied extensively to characterize materials in different forms, including solid, liquid, and gas phases. In the oil and gas industry, a spectral analysis had been employed to measure a mineralogy (Ballard [13]) and a reservoir fluid composition (Livanos et al., [14]). Typically, all of these measurements are prepared under an ambient or a low range of pressure conditions. For the present disclosure, high pressure IR cells with transparent windows (ZnSe for a maximum pressure of 2500 psi and sapphire for a maximum pressure of 5000 psi) were installed in line with a rock sample holder to capture a flow-through fluid signal. A Thermo-Scientific Nicolet 6700® FT-IR spectrometer (wavelength number ranges 600-4000 cm$^{-1}$) was used to continuously measure and analyze the flow-through fluid signal. A schematic of the experimental setup is presented in FIG. 1. During experiments, methane was diffused through the rock sample saturated with nitrogen, a constant pressure was maintained from both ends using the mercury displacement pump. The rock sample was confined with an effective pressure of 3000 psi.

Fourier Transform Infrared (FTIR) Spectroscopy Calibration

Figure 2:
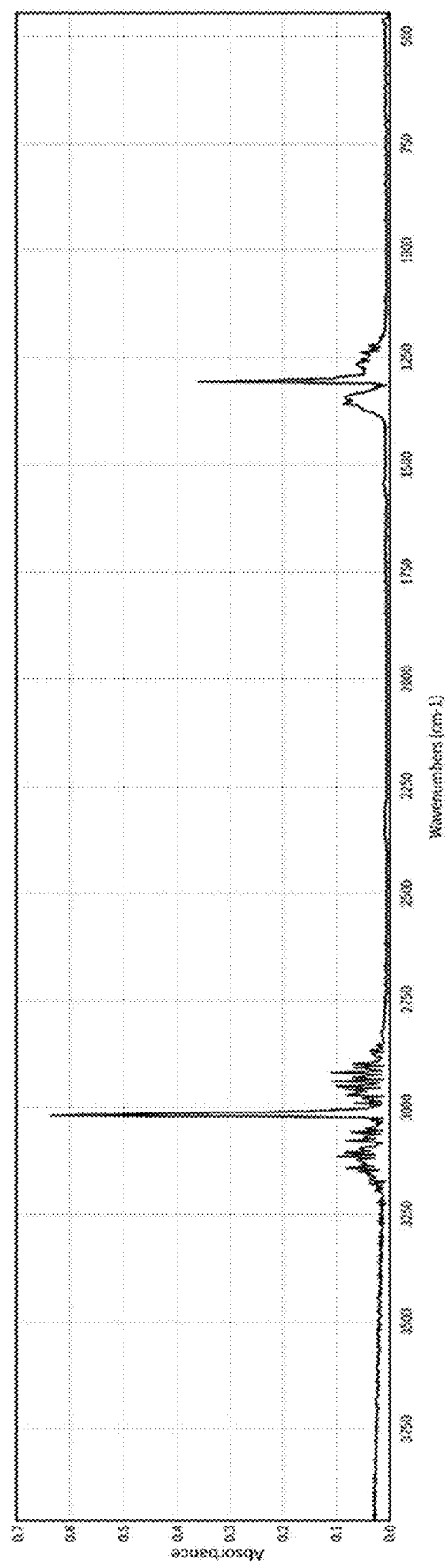
FIG. 2 shows a mid-range Fourier Transform Infrared (FTIR) absorbance spectrum of methane. The main absorbance range is from 2800-3100 $cm^{-1}$.

Throughout the diffusion process, a dynamic change of the fluid composition is due to an exchange of methane molecules and nitrogen molecules. In the present method, a single light beam is shot across the IR transparent window cells, wherein the spectrometer captures the IR absorbance intensity, which is due to a vibration of gas molecules between the IR transparent window cells. As a symmetric diatomic molecule, nitrogen does not yield an IR absorbance. On the other hand, a methane absorbance spectrum can easily be captured with a main absorbance range of 2800-3100 cm$^{-1}$ (FIG. 2, Nistchem Webbook [15]).

The Beer-Lambert law, shown in Equation (2), proposes a linear relationship between the IR absorbance intensity and the gas concentration. $C_o$, defined as the IR absorptivity coefficient of a particular gas, is a function of pressure and temperature. In this study, every experiment was executed at room temperature. Therefore, for a single diffusion test at a certain pressure, a methane concentration calibration needs to be provided.

$$A = l \sum_{i=1}^{N} \epsilon_i c_i \qquad \text{Eqn. 2}$$

Equation 2 provides a method for calculating the IR absorbance A, where l is the path length of the light beam through the IR transparent window cells, $\epsilon_i$ is an absorptivity of each of the gas components at a particular pressure-temperature condition, and $c_i$ is a concentration of each of the gas components within the gaseous phase.

Certain novel embodiments of the present disclosure, having now been generally described, will be more readily understood by reference to the following examples, which are included merely for purposes of illustration of certain aspects and embodiments of the present disclosure, and are not intended to be limiting. The following detailed examples are to be construed, as noted above, only as illustrative, and not as limiting of the present disclosure in any way whatsoever. Those skilled in the art will promptly recognize appropriate variations from the various compositions, structures, components, procedures and methods.

Methods and Results

Shown in FIG. 1 is a non-limiting embodiment of a diffusion assembly 10 for measuring gas diffusion through a rock sample in accordance with the present disclosure. The diffusion assembly 10 has a gas flooding system 12 and an Infrared spectroscopy system 14 constructed to have a first infrared spectrometer 14a and a second infrared spectrometer 14b. A first transparent window cell 16 is installed in the first infrared spectrometer 14a, which is configured to pass a first infrared beam 24 through the first transparent window cell 16. A second transparent window cell 18 is installed in the second infrared spectrometer 14b, which is configured to pass a second infrared beam 26 through the second transparent window cell 18. In some embodiments, the first transparent window cell 16 and the second transparent window cell 18 can be installed in a single infrared spectrometer. The gas flooding system 12 has an input end (gas inlet) 28 and an output end (gas outlet) 30. The gas flooding system 12 contains a sample vessel 20, configured to be pressurized and to hold a test sample 22. In some embodiments the test sample 22 can be a rock sample or a non-porous control (tube) sample. A confinement fluid 46 is injected into the gas flooding system 12 to apply a confinement stress to the test sample 22 contained within the sample vessel 20. A constant volume valve 32 is positioned upstream of the infrared spectrometry system 14 and is used to control gas flow into the infrared spectrometry system 14. A nitrogen gas source 38 provides nitrogen gas to the diffusion assembly 10 via a nitrogen inlet valve 40. A methane gas source 34 provides methane gas to the diffusion assembly 10 via a methane inlet valve 36. A mercury displacement pump 44 maintains hydraulic pressure in the diffusion assembly 10 throughout the experiment. In some embodiments, the mercury displacement pump 44 can be a vacuum pump. A plurality of measurements can be displayed, stored, and/or transmitted using computational/storage/communication resources that are integrated with the diffusion assembly 10 or determined by a remotely located server. In one non-limiting embodiment, the plurality of measurements can be displayed digitally on an output display 42.

Figure 3:
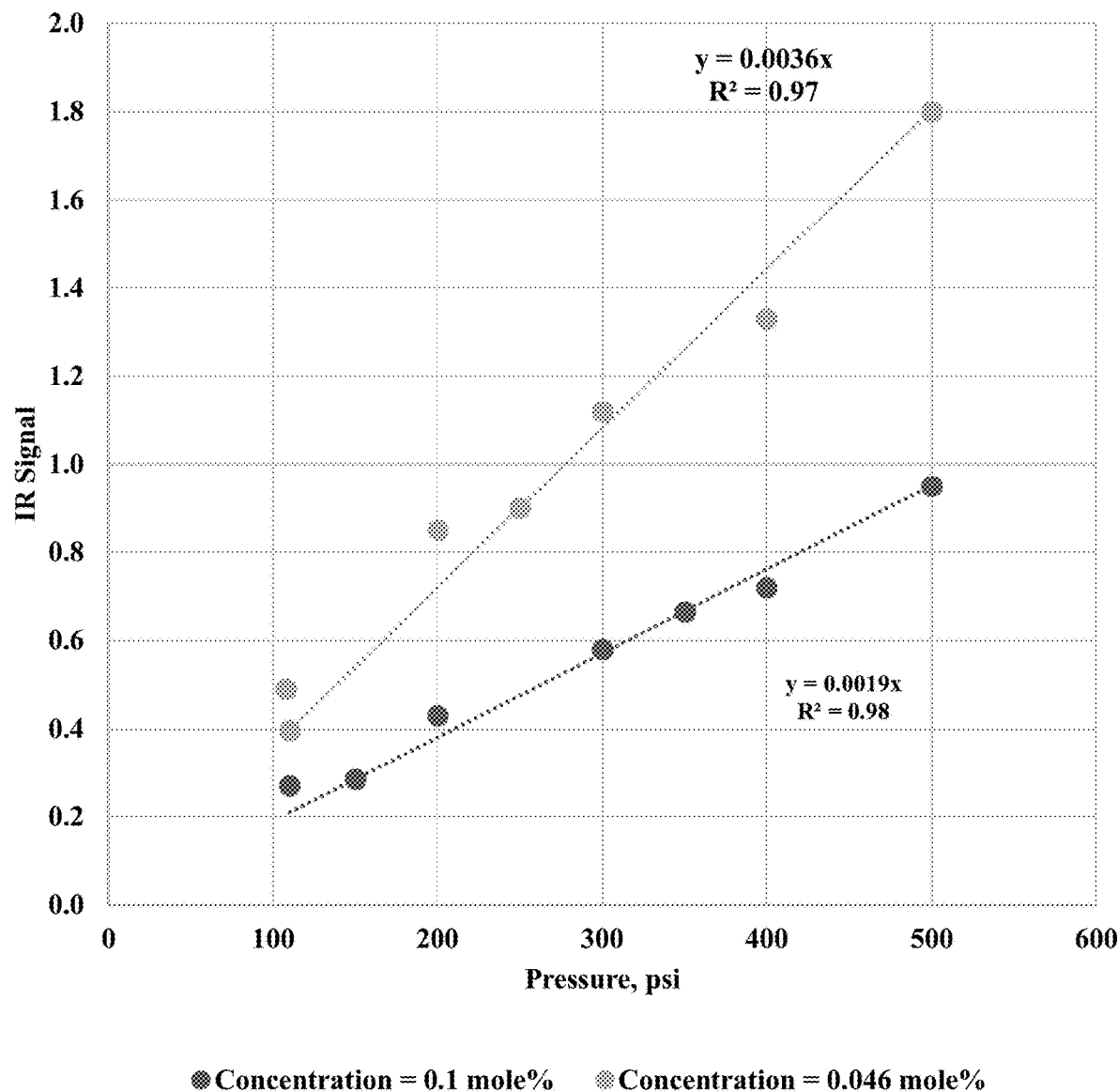
FIG. 3 shows an IR absorbance intensity of two methane-nitrogen gas mixtures at different pressures.
Figure 4:
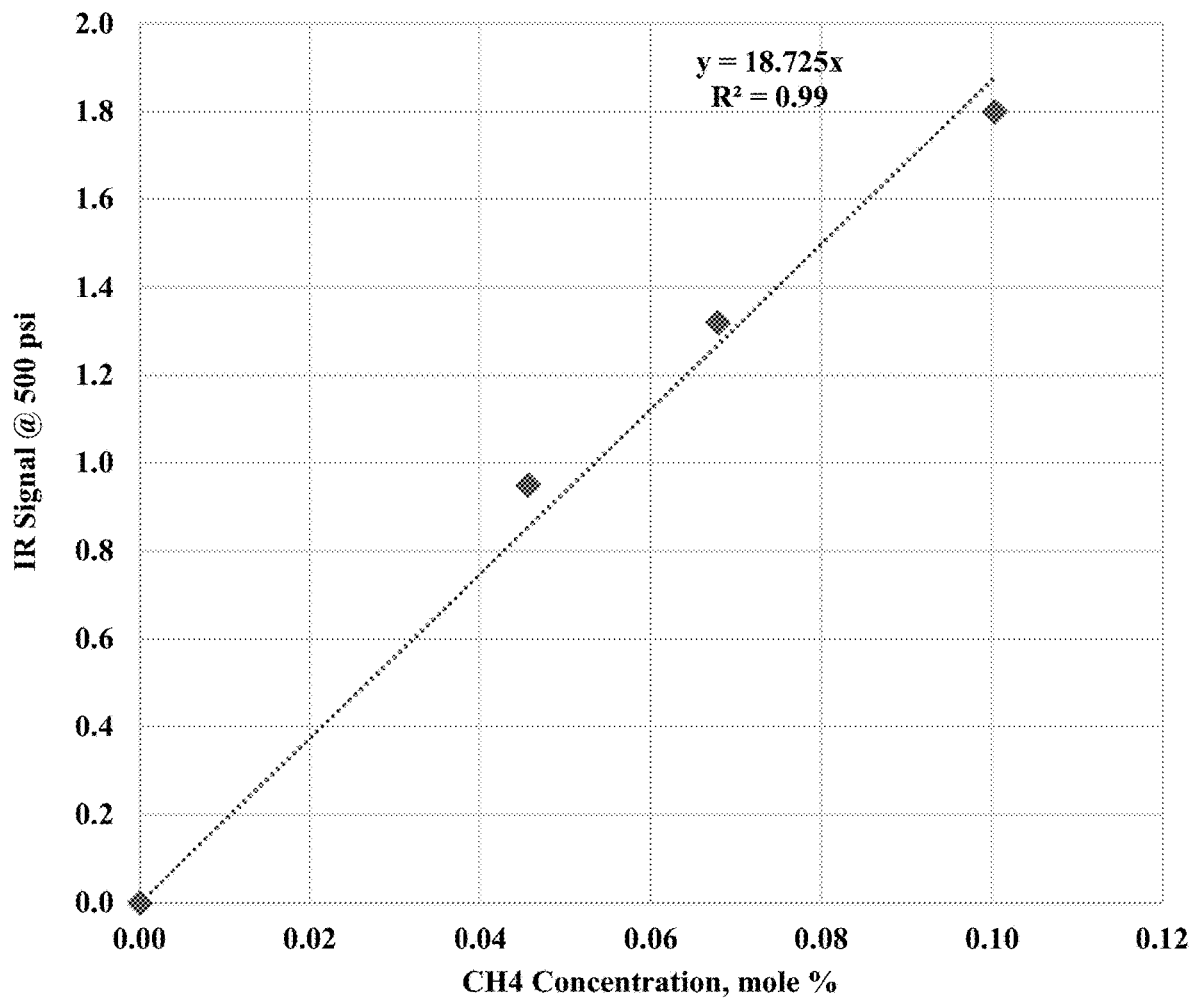
FIG. 4 shows an IR absorbance intensity of different methane-nitrogen gas mixtures at 500 psi, room temperature. The slope of linear correlation is considered the methane absorptivity, specifically at 500 psi.

A Rubotherm Flexidose® Gas mixer was used to generate three mixtures of methane and nitrogen with different concentrations. The three mixtures of methane and nitrogen were used to estimate the IR absorptivity coefficient at different pressures. FIG. 3 presents the relationship between the IR absorbance intensity versus the different pressures (pressure range from 100-500 psi) for different gas mixtures. FIG. 4 presents the relationship between the IR absorbance intensity versus a molar concentration of the methane at 500 psi. The slope of the linear correlation provides the methane absorptivity coefficient at 500 psi. Repeating the same procedure, the methane absorptivity coefficients are obtained at 200 psi and 300 psi. The methane absorptivity coefficients later were used to convert continuous IR absorbance spectra to a continuous methane concentration profile during the diffusion tests.

Figure 5:
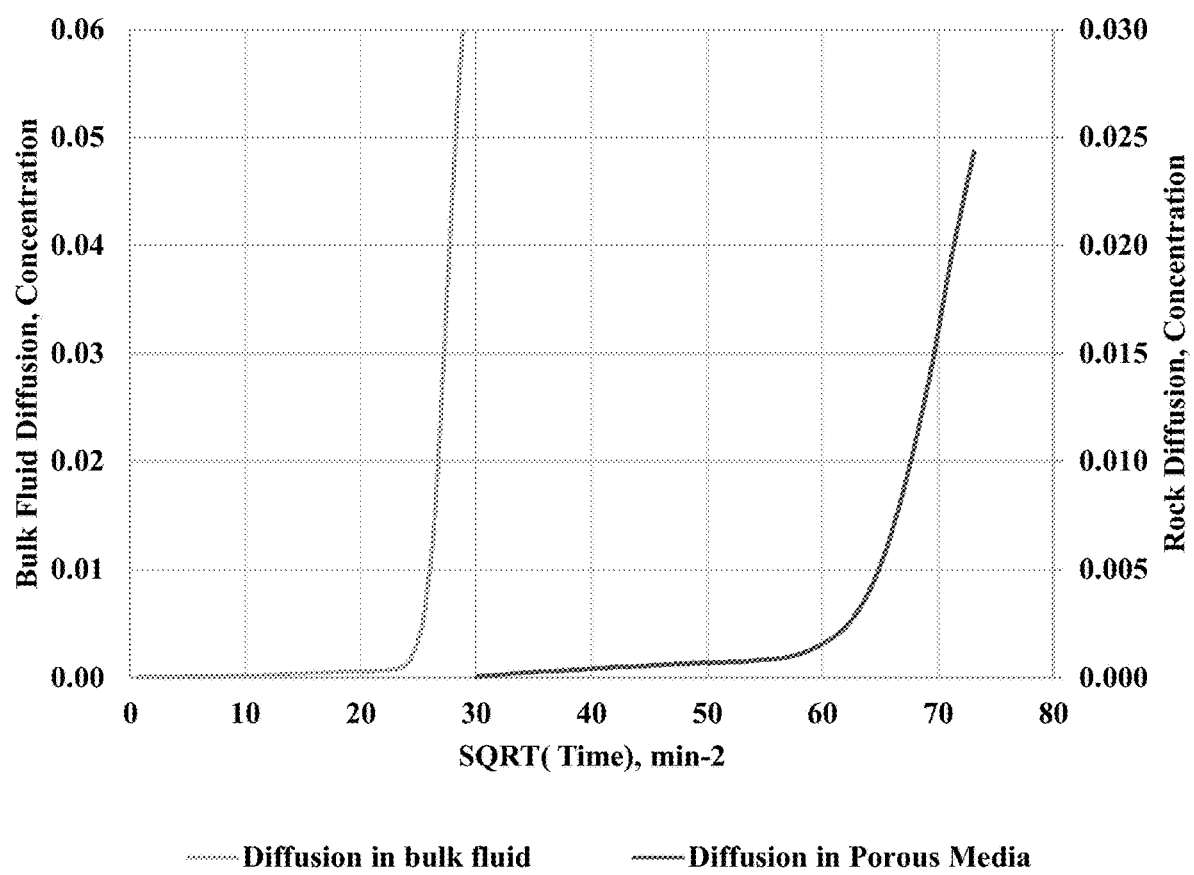
FIG. 5 shows methane concentration versus the square root of diffusion time. The left-hand curve is diffusion of a methane-nitrogen gas mixture through open space. The right-hand curve is diffusion of a methane-nitrogen gas mixture through a rock sample.
Figure 6:
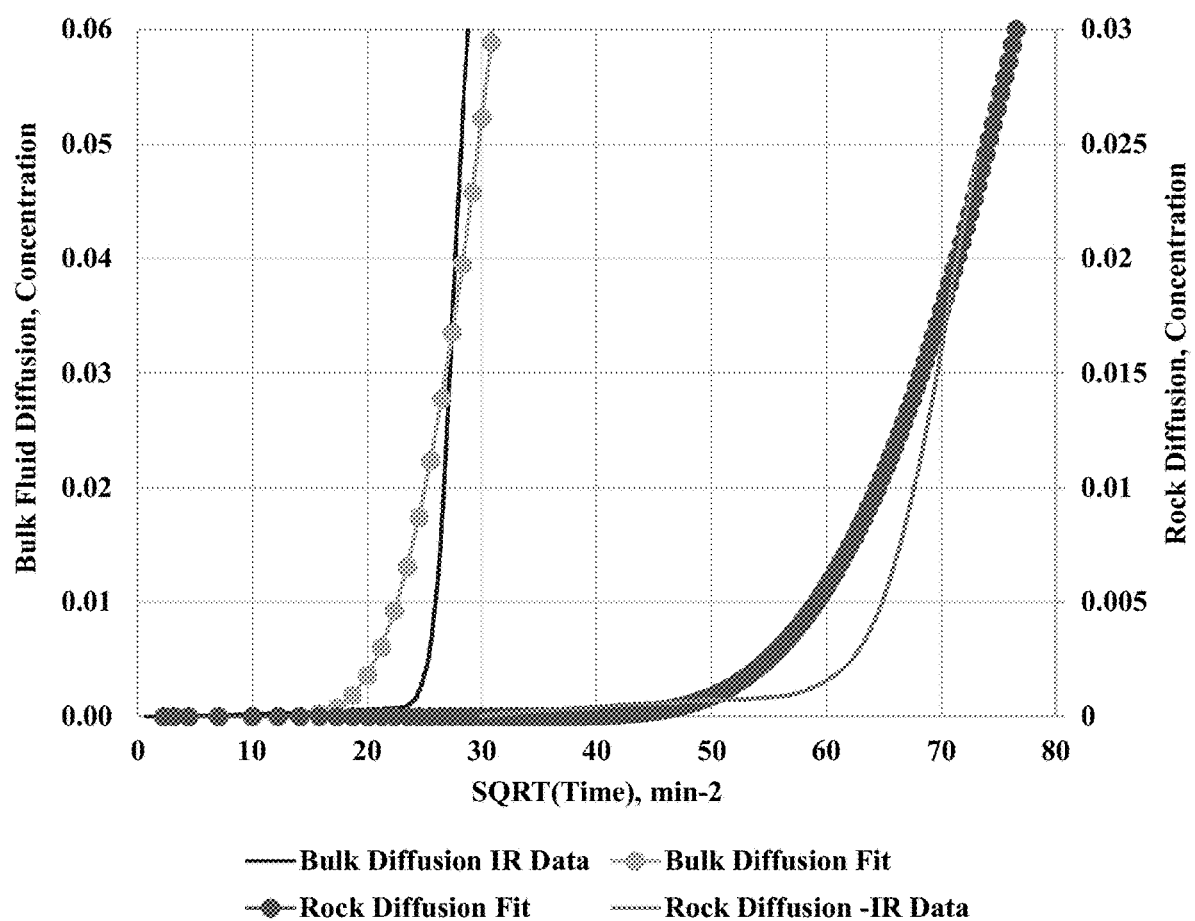
FIG. 6 shows methane-nitrogen diffusion through open space (left-hand curves) and a rock sample (right-hand curves). Solid lines are experimental data, while open circles are fit data calculated using Fick's second law of diffusion with effective diffusion coefficients of $3.25 \times 10^{-8}$ and $0.4 \times 10^{-8}$ $m^2/s$, respectively for bulk fluid diffusion and porous media diffusion.
Figure 7:
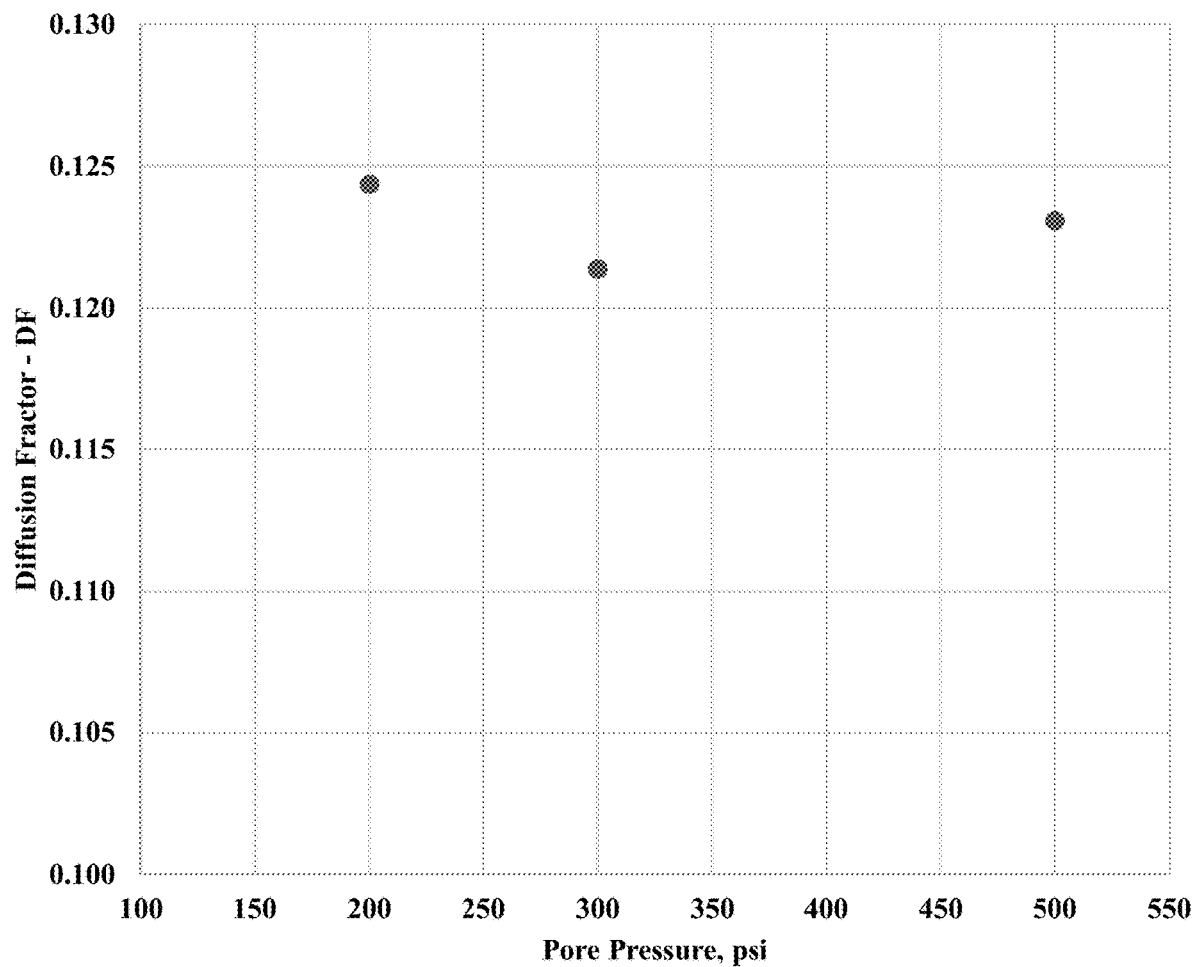
FIG. 7 shows the diffusion factor, or the ratio of the effective diffusion coefficient through a porous media to the diffusion coefficient through open space, is constant within a pore pressure range of 100-500 psi.

FIG. 5 presents methane concentration profiles versus the square root of time in minutes for a methane-nitrogen diffusion through a shale sample and the open space at a constant pressure of 500 psi. For the bulk methane-nitrogen diffusion process, the breakthrough time is about 450 mins; whereas for the diffusion within the shale sample, the breakthrough time is about 3600 mins. The maximum molar concentration of the methane at an end of each experiment (6400 minutes) is about 10%. With small concentrations, the conventional fluid sampling would not be able to provide a robust concentration profile for a diffusion rate calculation. Using Equation (1), the effective diffusion coefficient through the open space and the shale sample are estimated as $3.25*10^{-8}$ and $0.4*10^{-8}$ m$^2$/s, respectively. Applying the effective diffusion coefficients with the Fick's second law of diffusion, the continuous methane concentration profiles were generated, which agree well with the experimental data (FIG. 6). A diffusion factor is about 0.125 for the diffusion process at 500 psi. The diffusion factor data are presented in FIG. 7, as a function of the pressure. The diffusion factors calculated at different pressure points are the same with 90% confidence. The diffusion factor represents a tortuous characteristic of the porous media.

Figure 8:
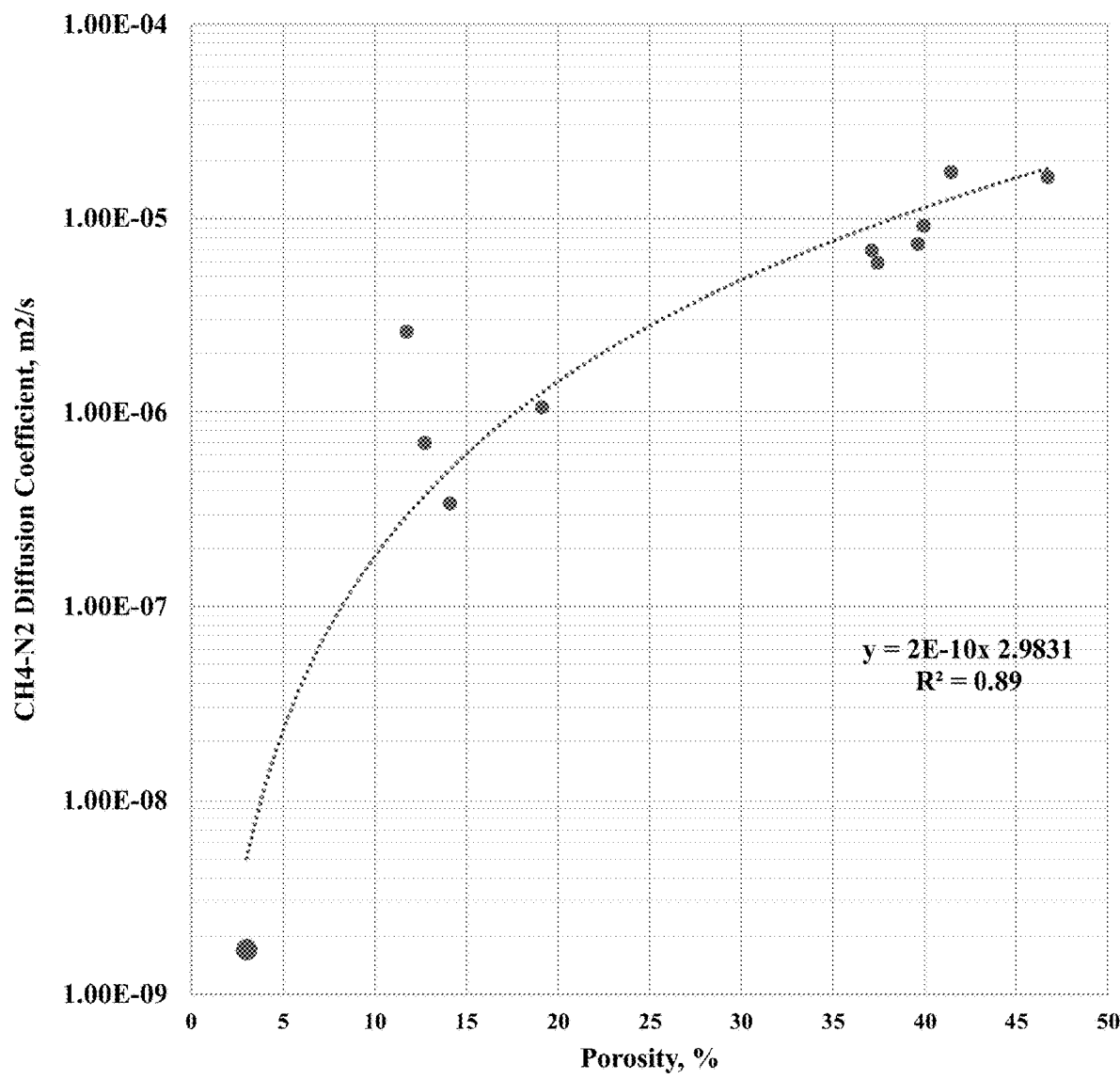
FIG. 8 shows an effective methane-nitrogen diffusion coefficient from the tight rock sample used in this study (with porosity of 3%) plotted against the literature data from Chen et al., 1977.
Figure 9:
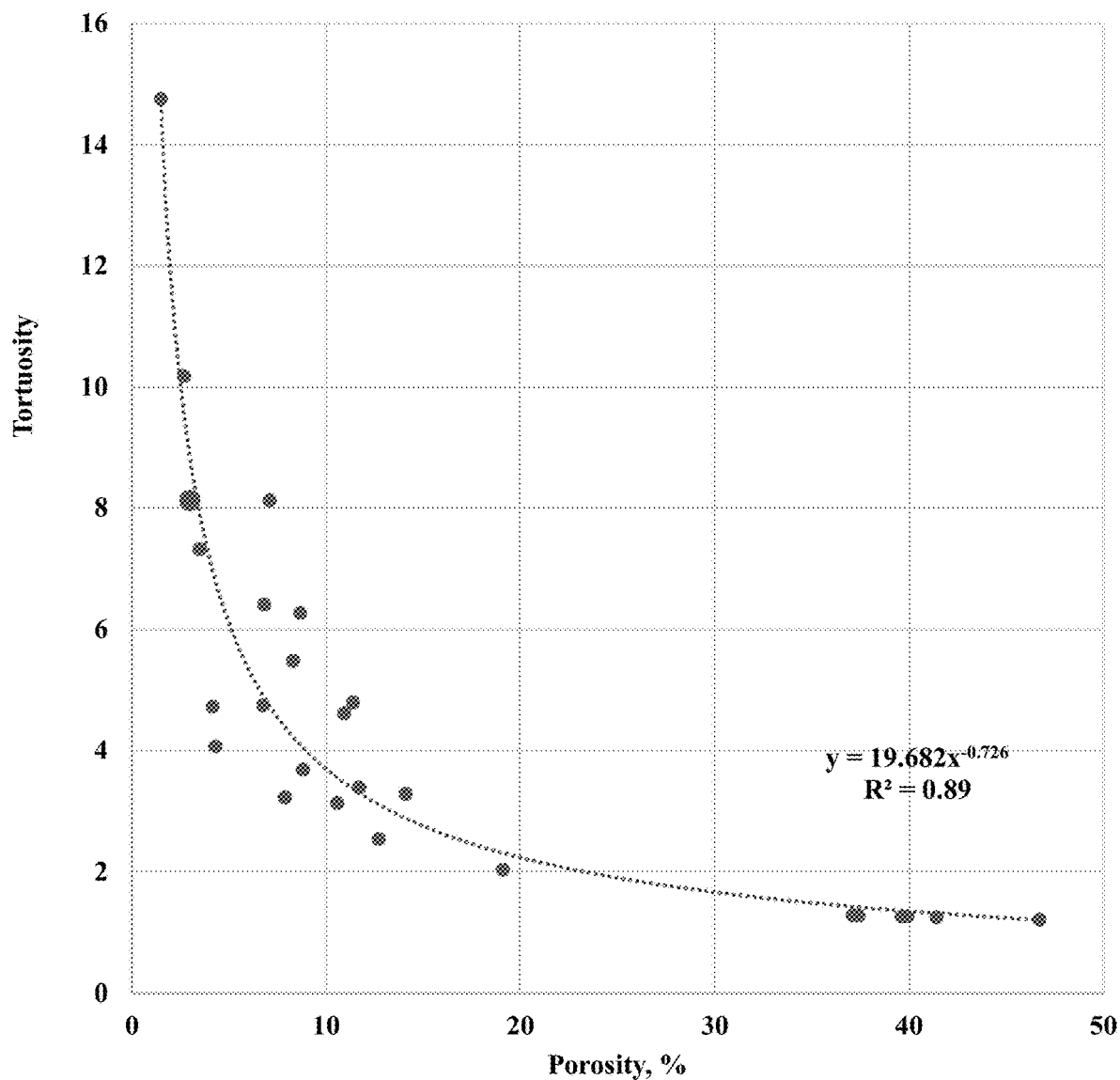
FIG. 9 shows dimensionless tortuosity, or the reverse of the diffusion factor—DF, from the tight rock sample used in this study (with porosity of 3%) plotted against the literature data from Chen et al., 1977.
Figure 10:
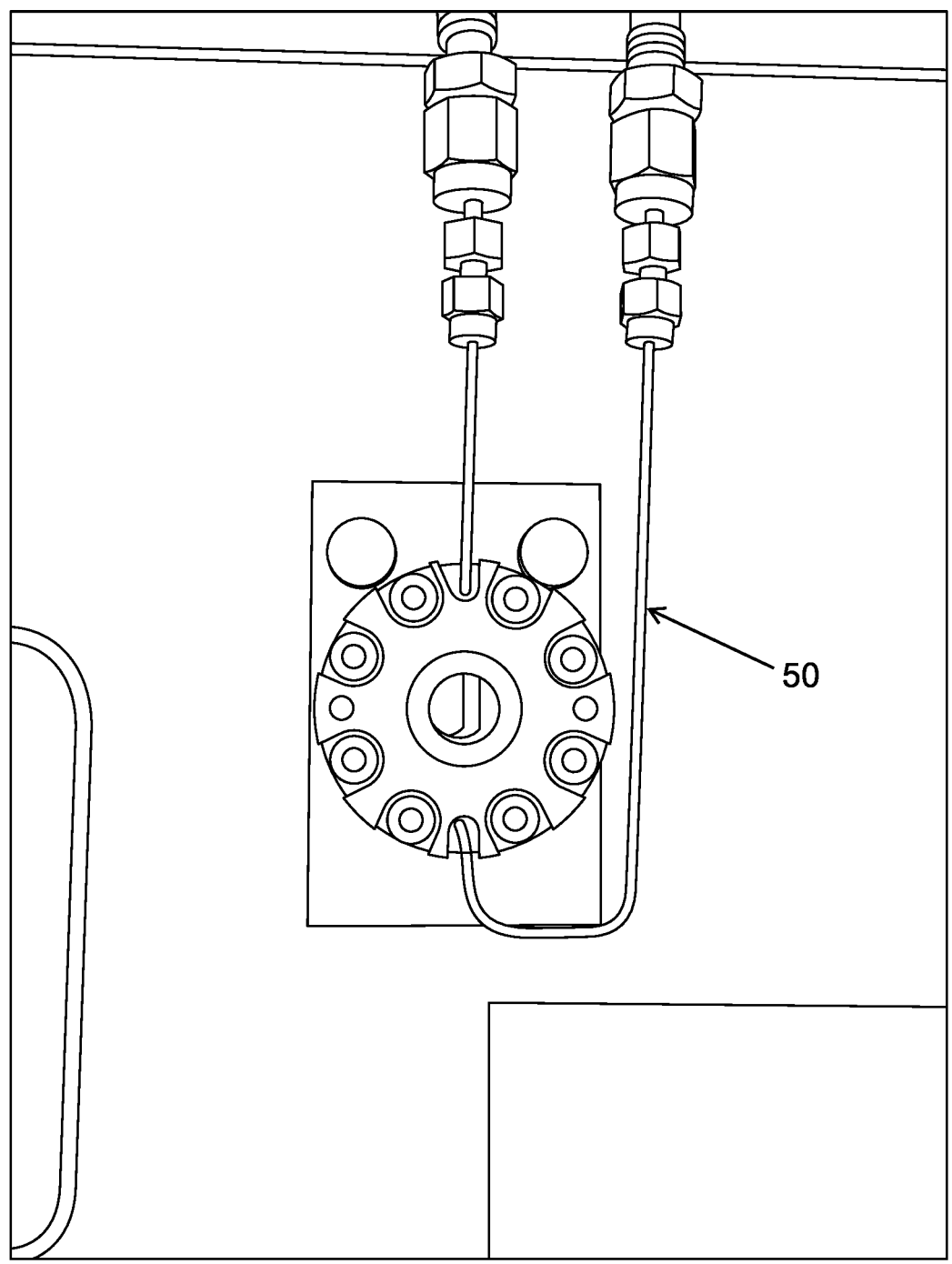
FIG. 10 shows an IR transparent window cell apparatus having a pressure grade of 5000 psi and for use at a temperature of 150° C.
Figure 11:
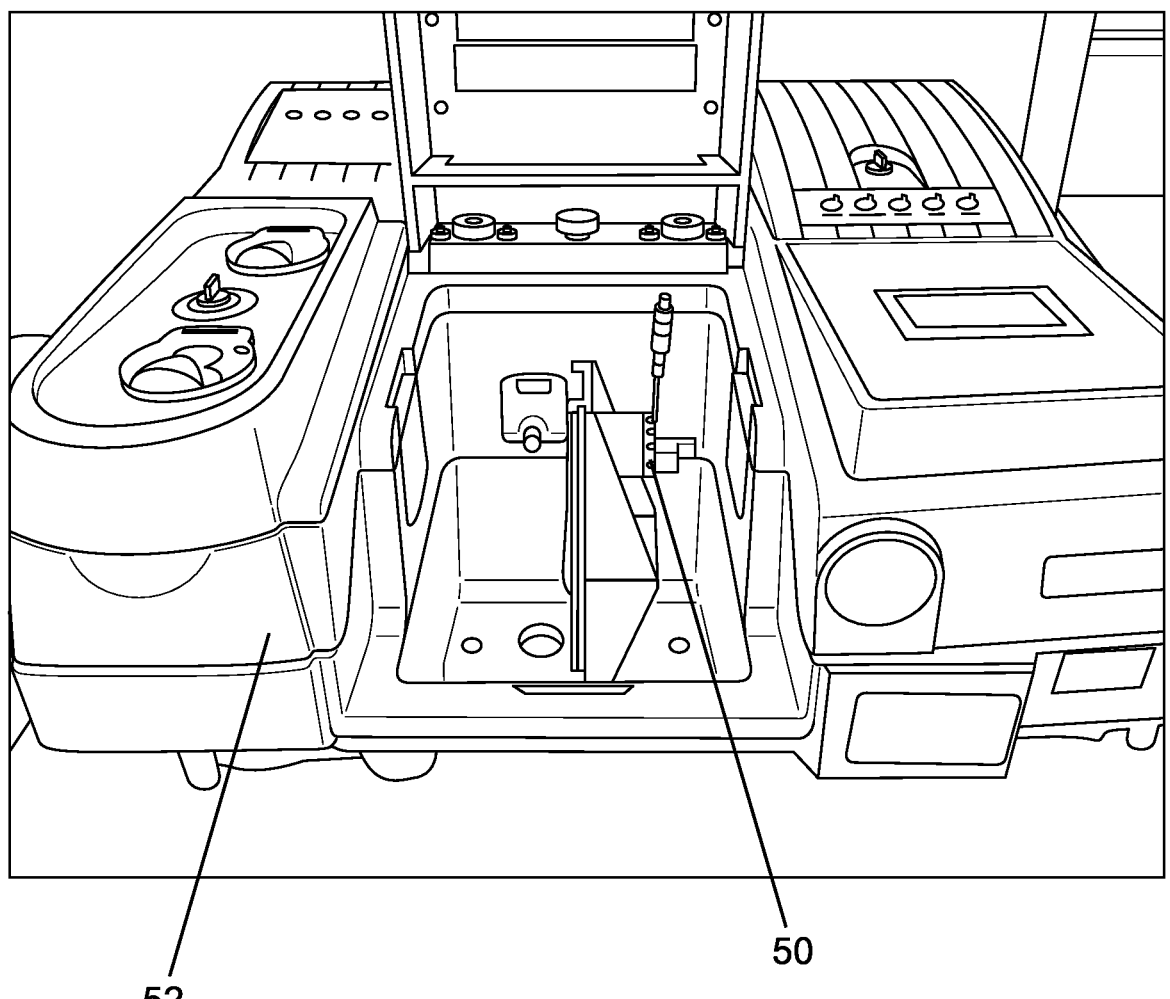
FIG. 11 shows an IR spectrometer with the IR transparent window cell apparatus of FIG. 10 installed.

The tortuosity of the shale sample is estimated as a reverse of the diffusion factor; the shale sample has a porosity of 3%. FIG. 8 shows the result plotted against the combined literature data. FIG. 9 shows a negative exponential correlation between the diffusion, the tortuosity, and the porosity. FIG. 10 shows an IR transparent window cell apparatus 50 having a pressure grade of 5000 psi and for use at a temperature of 150° C., and FIG. 11 shows an IR spectrometer 52 with the IR transparent window cell apparatus 50 of FIG. 10 installed therein.

In summary, despite the importance of diffusion as a transport mechanism in tight rock formations, such as shales, direct measurements of the effective diffusion coefficients have not been available, due in large part because of the small pore volume in the shale formations. The present disclosure describes a novel method and assembly for measuring the effective diffusion coefficient of gas compounds injected into shale rock samples. The effective diffusion between methane versus nitrogen were simultaneously measured with IR methods. The IR methods captured the change in the methane concentration and the nitrogen concentration at the inlet and outlet of a gas flooding system containing the shale rock sample as a function of time. The difference of the effective diffusion with and without the microporous media, provide the tortuosity of the shale rock sample. A simulation model was established based on the experimental setup to back-calculate the diffusion rate. A sequence of steps for estimating, in one non-limiting embodiment, the tortuosity and the effective diffusion coefficient in a low porosity-low permeability rock sample is shown below.

Step 1. Collect a rock sample from a drilling core. The rock sample is plugged to a cylindrical shape, such as OD=1 inch, and a length of 1 inch or longer. The longer the rock sample, the diffusion process is more pronounced, however, data acquisition time also increases. A suggested length of the rock sample is from 1 to 2 inches.

Step 2. A Soxhlet extraction may be required if the rock sample has a high bitumen/asphaltene concentration. The rock sample is then heated at 80° C. under a vacuum for 72 hours to remove movable in situ fluids inside the rock sample. Optionally, an Oxford Instrument GeoSpec2™ 12 MHz Nuclear Magnetic Resonance (NMR) spectrometer can be used to measure fluid saturation to confirm removal of the movable fluids.

Step 3. The rock sample is assembled in a gas flooding system, which is under a confinement stress. A minimum confinement stress is applied on the rock sample at 3,000 psi to minimize the effect of cracks/fractures within the rock sample. In a non-limiting embodiment, a rock sample pressure vessel is made of a Zirconium Oxide (ZrO), commercially available from Daedalus Innovations LLC (U.S. Pat. No. 9,983,277), and a confinement fluid is fluorinert. A maximum confinement pressure is 10,000 psi, and a maximum temperature is 120° C. Optionally, the rock sample pressure vessel is then arranged in the Oxford Instrument GeoSpec2™ 12 MHz NMR spectrometer. The ZrO and the fluorinert do not respond to NMR sequences, therefore, an NMR response during the experiment is solely due to an interaction of fluids and a porous system within the rock sample. Two IR transparent window cells are placed in the outlet and inlet ends of the gas flooding system to monitor to relative compositions of the injected gases. The IR transparent window cells may be made of zinc selenide (ZnSe) for 2000 psi grade (IR range 4000-600 cm$^{-1}$), or sapphire for 5000 psi grade (4000-1200 cm$^{-1}$). Thermo Scientific Nicolet 6700™ IR spectrometers may be used to conduct FTIR measurements in a transmission mode, data is collected every 30 seconds and stacked to create an IR profile as a function of time. FIG. 2 shows an exemplary IR spectrum at a single time frame of 30 seconds. Nitrogen and methane are used for the diffusion test; while nitrogen does not have an IR signal, an IR response is solely due to a change in the molar concentration of methane. Methane has two major adsorption bands, 3200-2800 cm$^{-1}$ and 1450-1250 cm$^{-1}$.

Step 4. The IR signal as a function of time corresponds to the molar concentration of methane in the binary mixture of methane and nitrogen. The FTIR Spectroscopy Calibration is performed to convert the IR absorbance intensity into a true concentration estimation, which will be used in Step 6. Different known gas mixtures comprising molar mixtures of methane-nitrogen are injected into an IR cell at a specific pressure, and the IR absorbance intensities are collected. Then, the correlation between the IR absorbance intensity and the concentration of methane is generated. This step is repeated for different pressures.

Step 5. The constant volume valve is closed. Nitrogen is flooded into the system at a specific head pressure; the rock sample is saturated with nitrogen until a nitrogen saturation process is complete. The nitrogen saturation process can take up to 1-3 days. After that, the constant volume valve is open, and methane is introduced into the flow system with the specific head pressure from the nitrogen saturation process. Pressures from both the nitrogen and methane inlet are carefully monitored to maintain a hydraulic balance. The IR spectrometers continuously record the change in concentration of methane in the binary mixtures in both the inlet and the outlet IR transparent window cells, thereby obtaining continuous methane concentration profiles.

Figure 12:
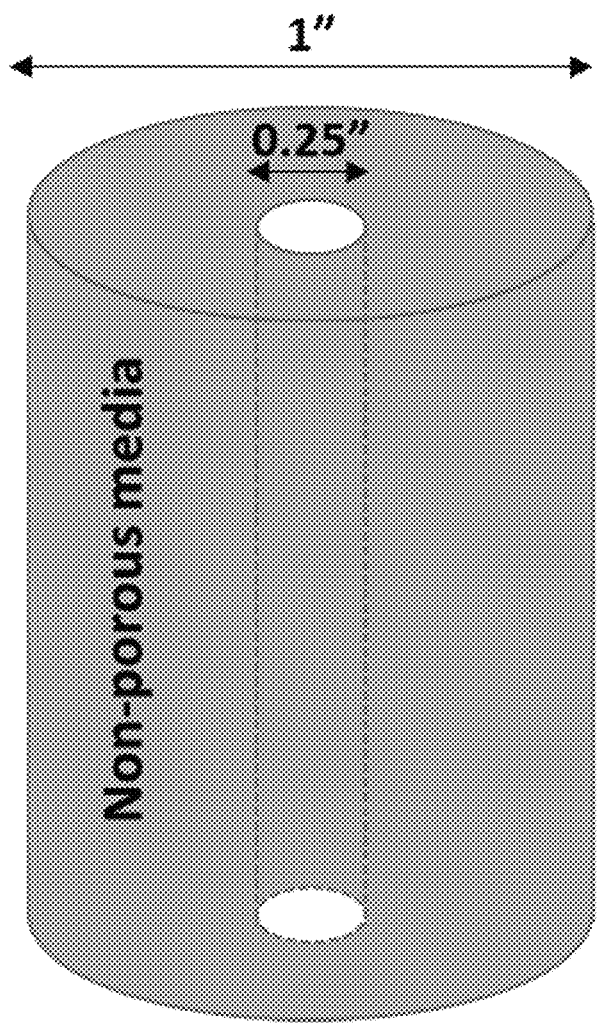
FIG. 12 shows the illustration of the standard tubing ("tube sample" or "control sample"), which is utilized along with the diffusion system to measure bulk fluid diffusivity between methane and nitrogen. As a straight tubing, its tortuosity is equal to 1. The tube can be made of non-porous material, such as stainless steel.

Step 6. The continuous methane concentration profiles are then fitted with Maxwell-Stefan equation and Fick's second law of diffusion to derive the effective diffusion coefficient ($D_e$) of the methane-nitrogen mixture through the porous media. The same experimental setup (Steps 3-6) can be repeated with a standard tubing which provides a control sample, instead of a porous rock sample, to estimate a bulk diffusion coefficient ($D_{12}$) of the methane-nitrogen mixture. In a non-limiting embodiment, the standard tubing (i.e., "tube sample") may be a drilled-through cylindrical sample, made of a non-porous material, such as a metal (e.g., stainless steel) with an outer diameter (OD) of e.g., 1 in, and an inner diameter (ID) of e.g., 0.25 in as shown in FIG. 12 for example. The ratio of the bulk diffusion coefficient to the effective diffusion coefficient is considered a tortuosity factor.

Further details of the methods and assembly for measuring the effective diffusion coefficient in the tight rock formations are shown in Appendix A of U.S. provisional application Ser. No. 62/721,775 filed Aug. 23, 2018.

While the present disclosure has been described in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure. Thus the examples described above, which include particular embodiments, will serve to illustrate the practice of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the presently disclosed methods. Changes may be made in various aspects of the methods described herein without departing from the spirit and scope of the present disclosure. The various elements, components, assemblies, and/or steps of the present disclosure may be combined or integrated in another system or certain features may be omitted, or not implemented. In addition, techniques, systems, subsystems, and methods described and illustrated in the various embodiments as discrete or separate may be combined or integrated with other systems, components, techniques, or methods without departing from the scope of the present disclosure. Other items shown or discussed as coupled may be directly coupled or communicating with each other or may be indirectly coupled or communicating through some interface, device, or intermediate component whether electrically, mechanically, or otherwise. Other examples of changes, substitutions, and alterations are ascertainable by one skilled in the art and may be made without departing from the spirit and scope disclosed herein

REFERENCES

Hill, E. S., and Lacy, W. N., 1934. Rate of solution of methane in quiescent liquid hydrocarbons. Ind. Eng. Chem. 26, 1324-1327.

Bertram, E. A., and Lacy, W. N., 1935. Rates of solution of gases in oils. Ind. Eng. Chem. 28, 316-318.

Reamer, H. H., Opfell, J. B., and Sage, B. H., 1956. Diffusion coefficients in hydrocarbon systems: methane-decane-methane in liquid phase. Ind. Eng. Chem. 48, 275-282.

Chen, L. L. Y., 1973. Binary Gas Diffusion of methane-nitrogen through porous media. Ph.D. Thesis, Univ. Mich.

Pandey, G. H., Katz, D. L., and Tek, M R., 1974. Diffusion of fluids through porous media with implications in petroleum geology. *American Association of Petroleum Geologists Bulletin*, 58, No. 2, 291.

Chen, M., Kang, Y., Zhang, T., You, L., Li, X., Chen, Z., Wu, K., and Yang, B., 2018. Methane diffusion in shales with multiple pore sizes at supercritical conditions. *Chemical Engineering Journal*, No. 334, 1455-1465.

Garrouch, A. A., Liaqat, A., and Fuad, Q., 2001. Using diffusion and electrical measurement to assess tortuosity of porous media. *Ind. Eng. Chem. Res*, No. 40, 4363-4369

Wicke, E., and Kallenbach R., 1941. Die Oberflachendiffusion von Kohlendioxyd in aktiven kohlen. *Kolloid Zeitshrtft*, 97, 135.

Evans R. B., Watson G. M., and Mason E. A., 1961. Gaseous diffusion in porous media at uniform pressure, *J. Chem. Phys*, 35, No. 6, 2076.

Chen, L. L. Y., Katz, D. L., and Tek, M. R., 1977. Binary gas diffusion of methane-nitrogen through porous media. AIChE Journal, Vol. 23, No. 3, 336.

Riazi, M. R., 1996. A new method for experimental measurement of diffusion coefficients in reservoir fluids. J. Pet. Sci. Eng. 14, 235-250.

Jamialahmadi, M., Emadi, M., and Muller-Steinhagen, H., 2006. Diffusion coefficients of methane in liquid hydrocarbons at high pressure and temperature. *Journal of Petroleum Science and Engineering*, No. 53, 47-60.

Ballard, B. D., 2007. Quantitative Mineralogy of Reservoir Rocks Using Fourier Transform Infrared Spectroscopy. Society of Petroleum Engineers. doi:10.2118/113023-STU.

Livanos, G., Zervakis, M., Pasadakis, N., Karelioti, M., and Giakos, G., 2016. Deconvolution of petroleum mixture using mid-MIR analysis and non-negative matrix factorization. *Measurement Science and Technology*, No. 27.

Wallace, W., *Methane Infrared Spectrum*, NIST Mass Spectrometry Data Center, NISTChemWebBook SRD. 69.

What is claimed is:

1. An assembly for measuring gas diffusion through a rock sample, comprising:

(1) a gas flooding system, (2) a first transparent window cell and a second transparent window cell, and (3) an infrared spectroscopy system, wherein, the gas flooding system comprises a sample vessel configured to contain the rock sample and is able to be pressurized to exert a confinement stress on the rock sample, the first transparent window cell is positioned to sample an input gas delivered to a gas inlet of the gas flooding system, and configured to monitor an input methane concentration profile of the input gas as a function of time as the input gas passes into the gas inlet of the gas flooding system, the second transparent window cell is positioned to sample an output gas outflowing from a gas outlet of the gas flooding system, and configured to monitor an output methane concentration profile of the output gas as a function of time as the output gas passes from the gas outlet of the gas flooding system, and the infrared spectrometry system is configured to continuously pass a first infrared beam through the first transparent window cell as the input gas passes therethrough, and a second infrared beam through the second transparent window cell as the output gas passes therethrough.

2. The assembly of claim 1, wherein the infrared spectrometry system comprises a first Fourier Transform Infrared (FTIR) spectrometer having the first transparent window cell, and a second FTIR spectrometer having the second transparent window cell.

3. The assembly of claim 1, wherein the sample vessel is constructed of zirconium oxide.

4. The assembly of claim 1, wherein the first transparent window cell and the second transparent window cell are constructed of zinc selenide or sapphire.

5. The assembly of claim 1, further comprising a vacuum pump, wherein the vacuum pump is configured to pressurize the gas flooding system.

6. A method for analyzing a rock sample, comprising:
providing a diffusion assembly comprising:
(1) a gas flooding system,
(2) a first transparent window cell and a second transparent window cell, and
(3) an infrared spectroscopy system,
wherein, the gas flooding system comprises a sample vessel configured to contain the rock sample and to be pressurized to exert a confinement stress on the rock sample,
the first transparent window cell is positioned to sample an input gas delivered to a gas inlet of the gas flooding system,
the second transparent window cell is positioned to sample an output gas outflowing from a gas outlet of the gas flooding system, and
the infrared spectrometry system is configured to continuously pass a first infrared beam through the first transparent window cell and a second infrared beam through the second transparent window cell for continuously monitoring dynamic changes in methane versus nitrogen concentrations in the input gas and the output gas;
providing the rock sample, wherein the rock sample has been obtained from a whole core traversing a formation;
positioning the rock sample within the sample vessel of the gas flooding system;
applying the confinement stress to the rock sample;
injecting nitrogen gas into the gas flooding system until the rock sample is saturated with nitrogen gas;
injecting an input of methane into the gas inlet of the gas flooding system and receiving an output mixture of methane and nitrogen from the gas outlet of the gas flooding system;
obtaining an input methane concentration profile of the input gas as a function of time as the input gas passes through the first transparent window cell;
obtaining an output methane concentration profile of the output gas as a function of time as the output gas passes through the second transparent window cell; and combining the input methane concentration profile and the output methane concentration profile to determine a measure of gas diffusion through the rock sample.

7. The method of claim 6, further comprising:
heating the rock sample under a vacuum for removing one or more in situ fluids from the rock sample prior to positioning the rock sample within the sample vessel of the gas flooding system.

8. The method of claim 6, wherein the infrared spectrometry system comprises a first Fourier Transform Infrared (FTIR) spectrometer having the first transparent window cell and a second FTIR spectrometer having the second transparent window cell.

9. The method of claim 6, wherein the sample vessel is constructed of zirconium oxide.

10. The method of claim 6, wherein the sample vessel is positioned in a nuclear magnetic resonance (NMR) spectrometer, and the methane concentration in the rock sample is directly monitored by the NMR spectrometer.

11. The method of claim 6, wherein the confinement stress is applied to the rock sample at a range between 3,000 psi and 10,000 psi.

12. The method of claim 6, wherein the confinement stress applied to the rock sample is at least 500 psi greater than a pore pressure applied by a mercury displacement pump.

13. The method of claim 6, wherein the first transparent window cell and the second transparent window cell are constructed of zinc selenide or sapphire.

14. The method of claim 6, wherein the diffusion assembly further comprises a confinement fluid.

15. The method of claim 14, wherein the confinement fluid is a non-conductive, fluorocarbon-based fluid.

16. The method of claim 6, wherein the measure of the gas diffusion is an effective coefficient of diffusion of nitrogen and methane gas through the rock sample.

17. The method of claim 16, wherein the effective coefficient of diffusion of the nitrogen and methane gas through the rock sample is calculated using Maxwell-Stefan equation and Fick's second law of diffusion.

18. The method of claim 6, further comprising:
conducting an Infrared spectroscopy calibration test on the rock sample.

19. The method of claim 18, wherein the Infrared spectroscopy calibration test is a Fourier Transform Infrared Spectroscopy Calibration configured to measure an Infrared absorbance intensity of methane in the gas flooding system.

20. The method of claim 6, further comprising:
positioning, when the sample vessel is empty, a control sample into the sample vessel of the gas flooding system, wherein the control sample is non-porous and has a tubular inner channel extending longitudinally therethrough;
applying the confinement stress to the control sample in the sample vessel of the gas flooding system;
injecting nitrogen gas into the gas flooding system until the control sample is saturated with nitrogen gas;
injecting an input of methane into the gas inlet of the gas flooding system and receiving an output mixture of methane and nitrogen from the gas outlet of the gas flooding system;
obtaining a control input methane concentration profile of the input gas as a function of time as the input gas passes through the first transparent window cell;
obtaining a control output methane concentration profile of the output gas as a function of time as the output gas passes through the second transparent window cell;

combining the control input methane concentration profile and the control output methane concentration profile to determine a measure of gas diffusion through the control sample; and determining a measure of a tortuosity of the rock sample by calculating the ratio of the measure of gas diffusion through the control sample to the measure of gas diffusion through the rock sample.

21. The method of claim 20, wherein the control sample is defined as having a tortuosity value of 1.

* * * * *